United States Patent [19]

de Lauzon et al.

[11] 4,404,147

[45] Sep. 13, 1983

[54] PROCESS FOR THE SYNTHESIS OF 1,1-DIPHOSPHAFERROCENES

[75] Inventors: Guillaume de Lauzon; François Mathey, both of Paris, France

[73] Assignee: Societe Nationale des Poudres et Explosifs, Paris, France

[21] Appl. No.: 326,615

[22] Filed: Dec. 2, 1981

[30] Foreign Application Priority Data

Dec. 10, 1980 [FR] France ............................. 80 26168

[51] Int. Cl.$^3$ ............................................. C07F 17/02
[52] U.S. Cl. ............................................. 260/439 CY
[58] Field of Search ................................. 260/439 CY

[56] References Cited

U.S. PATENT DOCUMENTS 4,152,344  5/1979  Unruh ........................ 260/439 CY
4,201,714  5/1980  Hughes ..................... 260/439 CY X Primary Examiner—Helen M. S. Sneed
Attorney, Agent, or Firm—Bucknam and Archer

[57] ABSTRACT

The invention relates to the manufacture of 1,1'-diphosphaferrocenes.

The process consists of reacting a mixture of an alkali metal phenyl and an alkali metal phospholyl in the presence of a Lewis acid, in a basic ether, preferably at between $-20°$ and $+20°$ C., and then reacting the product obtained with ferrous chloride.

The process according to the invention is useful for lowering the production cost of 1,1'-diphosphaferrocenes.

9 Claims, No Drawings

PROCESS FOR THE SYNTHESIS OF 1,1-DIPHOSPHAFERROCENES

The present invention relates to the field of the manufacture of the phosphorus homologues of ferrocene derivatives, and more particularly of 1,1'-diphosphaferrocenes.

1,1'-Diphosphaferrocenes are compounds known for their high stability. In Journal of Organometallic Chemistry, 156 (1978) C 33–C 36, de Lauzon, Mathey and Simalty have described a process for the synthesis of these compounds, which consists of reacting a lithium phospholyl with anhydrous ferrous chloride according to the equation:

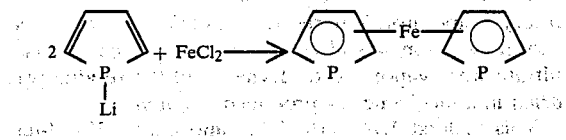

However, the yield of this process is not satisfactory because it is of the order of only 15%, the nature of the substitution pattern of the phospholyl nucleus being of little importance.

More recently, in Journal of American Chemical Society, 102, 994 (1980), de Lauzon et al. have described another method of obtaining these compounds, which consists of exchanging the sodium in sodium 3,4-dihydrocarbylphospholyl for magnesium, and then in reacting the magnesium compound obtained with anhydrous ferrous chloride. The yield of this process is a distinct improvement compared with the previous yield because it is of the order of 50%, but it is reached at the expense of a difficult separation of the final product from the reaction medium.

There is therefore an urgent need for a process which makes it possible to obtain 1,1'-diphosphaferrocenes with a good yield and without isolation difficulties. It is this need which the present invention proposes to satisfy.

The invention consists of a process for the synthesis of 1,1'-diphosphaferrocenes of the general formula:

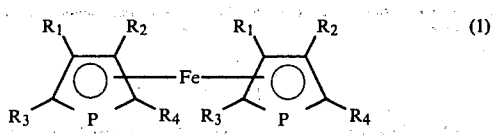

in which $R_1$, $R_2$, $R_3$ and $R_4$ are $C_1$ to $C_6$ alkyl groups, $C_6$ to $C_{12}$ aryl groups, $C_7$ to $C_{12}$ alkaryl groups, $C_7$ to $C_{12}$ aralkyl groups or a hydrogen atom, it being possible for $R_1$, $R_2$, $R_3$ and $R_4$ to be identical, by reacting anhydrous ferrous chloride with a mixture of a substituted alkali metal phospholyl and an alkali metal phenyl, characterised in that, before reacting the ferrous chloride with the mixture, the latter is treated with a Lewis acid.

A wide variety of Lewis acids has led to a substantial improvement in the yield, compared with the earlier processes. Metal salts which accept an electron pair are preferred and, amongst these, the following are even more particularly preferred: the halides of the metals of column 2b, in particular $ZnCl_2$ and $ZnI_2$, the halides of the metals of column 3a, in particular $BF_3 \cdot Et_2O$ and $AlCl_3$, the halides of the metals of column 4a, in particular $SnCl_4$, the halides of the metals of column 4b, in particular $TiCl_4$ and $ZrCl_4$, the halides of the metals of column 5a, in particular $SbF_3$ and $SbCl_3$, and the halides of the metals of column 5b, in particular $TaCl_5$ and $NbCl_5$.

It is possible to use either a single Lewis acid, which is preferable, or a mixture of Lewis acids. The amount of Lewis acid to be used is between one and three times the stoichiometric amount for neutralisation of the alkali metal phenyl. The yield of the reaction is sensitive to the proportion of Lewis acid relative to the alkali metal phenyl. It is recalled that, as described in the abovementioned publications, the mixture of the alkali metal phenyl and the alkali metal phospholyl used as the starting material in the present reaction is essentially equimolecular because it is prepared according to the equation:

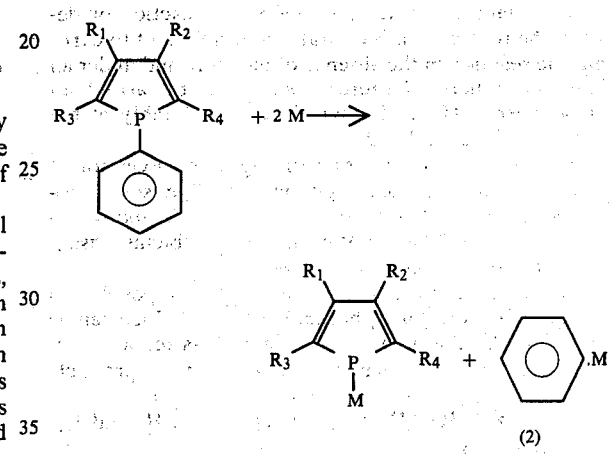

in which $R_1$, $R_2$, $R_3$ and $R_4$ have the abovementioned meanings and in which M is an alkali metal chosen from the group comprising lithium, sodium and potassium, it being possible for this alkali metal to be in a common solubilised form such as a radical anion like sodium naphthalide.

It has been found that, by applying the process according to the invention varying the proportion of Lewis acid, at least one yield maximum is observed, which corresponds to using the amount of acid required for neutralisation of the alkali metal phenyl,

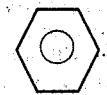

For example, if $AX_n$ represents a Lewis acid which is preferred according to the invention, that is to say a halide $(X^-)$ of an n-valent metal (A) belonging to one of the abovementioned columns, a yield maximum is observed when using 1/n mol of this Lewis acid per mol of alkali metal phenyl.

The fact that the Lewis acid first neutralises the alkali metal phenyl has been checked by $^{31}P$ NMR in a specific case: the addition of a third of a mol of $AlCl_3$ to a molar mixture of lithium 3,4-dimethylphospholyl and lithium phenyl in THF does not perturb the phosphorus signal due to the lithium phospholyl ($^{31}P = 56$ ppm) and does not produce any other signal corresponding to a new phosphorus species.

Generally, although not systematically, a second yield maximum is observed, which corresponds to twice the amount of Lewis acid required for neutralisation of the alkali metal phenyl, that is to say preferably $2/n$ mols of $AX_n$ per mol of alkali metal phenyl. Those skilled in the art can easily determine themselves, according to the starting mixtures and the type of Lewis acid, the proportion of Lewis acid which leads to the best yields, and can choose, for example, to use either $1/n$ or $2/n$ mols of $AX_n$ per mol of alkali metal phenyl.

According to the invention, the reaction is carried out in a solvent medium comprising a basic, inert and aprotic ether. Preferably, the solvent medium is not composed only of a solvent of this type. Tetrahydrofuran (THF) is a suitable solvent, but it is also possible to use a 10% strength mixture of THF in a hydrocarbon such as hexane or benzene. Glymes and diglymes are also satisfactory.

As certain impurities can inhibit the reaction or destroy the reactants, it is desirable and sufficient to carry out the reaction in the absence of moisture and under an inert atmosphere. The actual reaction can be carried out at between $-80°$ and $+50°$ C. and preferably at between $-20°$ C. and $+20°$ C.

By virtue of the process according to the invention, it is now possible to reach high yields of diphosphaferrocenes, which are frequently more than 50% and sometimes equal to 70%, without difficult problems arising when the final product is isolated.

Furthermore, the invention also makes it possible to broaden the range of diphosphaferrocenes which can be synthesised. Thus, by virtue of the process according to the invention, it has been possible to obtain the products of the general formula (I) in which $R_1=R_2=R_3=R_4=H$ and in which $R_1=CH_3$ and $R_2$, $R_3$ and $R_4=H$.

In general, the process according to the invention gives better results with the products in which $R_3=R_4=H$ and in which at least one of the radicals $R_1$ and $R_2$ is a hydrocarbyl group. However, the introduction of substituents in the X-positions ($R_3$, $R_4$) does not present any problem because, according to Journal of American Chemical Society, 102, 994 (1980), op.cit., it is possible to introduce them by electrophilic substitution after the diphosphaferrocene structure has been formed.

Finally, it must be noted that the Lewis acids used have a stabilising effect on the 1,1'-diphosphaferrocenes, which, together with the selected neutralisation of the alkali metal phenyl in the reaction medium, makes it possible to obtain the substantial improvements in yield which are observed within the scope of the invention. By virtue of the invention, it can be envisaged to make wider use of diphosphaferrocenes, which are useful in particular as light stabilisers for polymers.

Finally, the invention relates to 3-monomethyl-1,1'-diphosphaferrocene as a new product.

The value of the process according to the invention, and also the general nature of its application, will be appreciated even more clearly with the aid of the following non-limiting examples:

EXAMPLE 1

Synthesis of 3,3',4,4'-tetramethyl-1,1'-diphosphaferrocene 3 ml (3.15 g/16.7 mols) of 3,4-dimethyl-1-phenylphosphole were dissolved in 50 ml of THF. 353 mg of lithium were added to this solution and the mixture was stirred for 4 hours, the temperature being kept at 20° C. The reaction mixture was filtered and 133 mg of lithium were recovered, which corresponds to a yield of 94% for this preparatory step. 0.75 g (5.6 mols) of aluminium chloride were added to the resulting equimolecular mixture of lithium phenyl and lithium 3,4-dimethylphospholyl, cooled to 0° C. beforehand. The new mixture was stirred for 30 minutes at 0° C. and then for 30 minutes at 20° C. 1.1 g (8.6 millimols) of ferrous chloride were added to the mixture obtained, after which the medium was stirred for 12 hours at 20° C. After hydrolysis with 50 ml of 2 N HCl, the mixture was poured into 200 ml of hexane. The aqueous phase was separated off by decantation and the organic phase was washed with water and then dried over sodium sulphate. The volatile compounds were driven off on a rotary evaporator. The residue was taken up in hexane and the solution was filtered on a bed of silica gel. The filtrate was evaporated to dryness and the residue was dried in a mechanically produced vacuum.

This yielded 1.74 g (6.25 millimols) of 3,3',4,4'-tetramethyl-1,1'-diphosphaferrocene, which corresponds to a yield of 74%, relative to the phosphole used.

EXAMPLES 2 TO 9

The procedure of Example 1 was repeated in its entirety, except as regards the nature and/or the amount of the Lewis acid. The results obtained are provided in the following table, which shows the Lewis acid used, the amount of this acid used, the mass of product obtained and the corresponding yield.

| Example | Lewis acid | Amount in g (millimols) | Mass of product obtained in g (millimols) | Yield in % |
|---|---|---|---|---|
| 2 | AlCl$_3$ | 1.85 (13.8) | 1.36 (4.9) | 59 |
| 3 | ZnCl$_2$ | 1.13 (8.35) | 1.42 (5.1) | 61 |
| 4 | ZnCl$_2$ | 3.4 (25) | 1.46 (5.25) | 62 |
| 5 | ZnI$_2$ | (a) | 1.40 (5.0) | 61 |
| 6 | SbF$_3$ | 1.0 (4.1) | 1.20 (4.3) | 51 |
| 7 | SnCl$_4$ | 1.08 (4.1) | 1.12 (4.0) | 48 |
| 8 | BF$_3$—Et$_2$O | 0.78 (5.5) | 1.00 (3.6) | 43 |
| 9 | TiCl$_4$ | 0.79 (4.2) | 0.75 (2.7) | 32 |

(a) prepared from 6.4 g of iodine (25 millimols) and excess zinc (removed by filtration).

EXAMPLE 10

The procedure of Example 1 was applied to the synthesis of 3-methyl-1,1'-diphosphaferrocene, the only difference being the adoption of a temperature of 0° C. during the reaction with FeCl$_2$.

3.21 g (18.4 millimols) of 3-methyl-1-phenylphosphole, 70 ml of THF, an excess of lithium, 0.82 g (6.1 millimols) of AlCl$_3$ and 1.17 g (0.2 millimol) of FeCl$_2$ were used.

1.0 g (4 millimols) of 3-methyl-1,1'-diphosphaferrocene was isolated, which corresponds to a yield of 43%.

This product, which is new, was characterised by its NMR and mass spectra.

$^1$H NMR spectrum (CDCl$_3$)
 $\delta=2.15$ (s, 6H, Me)
 $\delta=3.68$ (d, $^2$J(H—P): 36 Hz, 2H, HC$_2$)
 $\delta=3.70$ (d×m, $^2$J (H—P): 38 Hz, 2H, HC$_5$)
 $\delta=5.05$ (m, 2H, HC$_4$)
(the $\delta$ values are expressed in ppm).

$^{31}$P NMR spectrum (CDCl$_3$) (external reference: phosphonic acid, δ: +at low field): a multiplet centered at −61.5 ppm was observed.

Mass spectrum (70 eV, 120° C.)
m/e=250 (M, 100%)
m/e=235 (M minus CH$_3$, 2.5%)
m/e=186 (2%)
m/e=153

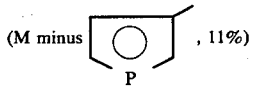

m/e=152 (12%)
m/e=139 (5%)
m/e=125 (M++, 2%)
m/e=108 (2%)
m/e=97

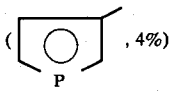

m/e=56 (Fe, 4%).

We claim:

1. Process for the synthesis of 1,1'-diphosphaferrocenes of the general formula:

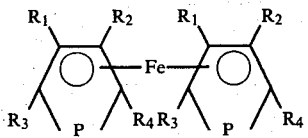

in which R$_1$, R$_2$, R$_3$ and R$_4$ are C$_1$ to C$_6$ alkyl, C$_6$ to C$_{12}$ aryl, C$_7$ to C$_{12}$ alkaryl, C$_7$ to C$_{12}$ aralkyl or a hydrogen atom, R$_1$, R$_2$, R$_3$ and R$_4$ being the same or different, by reacting anhydrous ferrous chloride with a mixture of equimolar amounts of a substituted alkali metal phospholyl and an alkali metal phenyl, wherein before reacting the ferrous chloride with the mixture, the latter is treated with a Lewis acid at a temperature between −80° C. and +50° C.

2. Process of synthesis according to claim 1, wherein the Lewis acid is a metal salt which accepts an electron pair.

3. Process of synthesis according to claim 2, wherein the metal salt which accepts an electron pair is a member selected from the group consisting of the halides of the metals of column 2b, the halides of the metals of column 3a, the halides of the metals of column 4a, the halides of the metals of column 4b, the halides of the metals of column 5a and the halides of the metals of column 5b.

4. Process of synthesis according to claim 3, wherein the metal salt which accepts an electron pair is a member selected from the group consisting of ZnCl$_2$, ZnI$_2$, BF$_3$Et$_2$O, AlCl$_3$, SnCl$_4$, TiCl$_4$, ZrCl$_4$, SbF$_3$, SbCl$_3$, TaCl$_5$ and NbCl$_5$.

5. Process of synthesis according to claim 1, wherein an amount of Lewis acid of between one and three times the stoichiometric amount for neutralisation of the alkali metal phenyl is used.

6. Process of synthesis according to claim 1, wherein the reaction is carried out in a solvent medium comprising a basic, inert and aprotic ether.

7. Process of synthesis according to claim 6, wherein the basic, inert and aprotic ether is THF.

8. The compound 3-monomethyl-1,1'-diphosphaferrocene.

9. The process according to claim 1, wherein the temperature is between −20° C. and +20° C.

* * * * *